(12) United States Patent
Seitz

(10) Patent No.: US 6,252,108 B1
(45) Date of Patent: Jun. 26, 2001

(54) METHOD FOR PRODUCING ALUMINIUM SALTS OF CYCLIC PHOSPHINIC ACID

(75) Inventor: Thomas Seitz, Heddesheim (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/485,198

(22) PCT Filed: Aug. 3, 1998

(86) PCT No.: PCT/EP98/04833

§ 371 Date: Feb. 4, 2000

§ 102(e) Date: Feb. 4, 2000

(87) PCT Pub. No.: WO99/07715

PCT Pub. Date: Feb. 18, 1999

(30) Foreign Application Priority Data

Aug. 7, 1997 (DE) .............................. 197 34 246

(51) Int. Cl.$^7$ ...................................... C07F 9/30
(52) U.S. Cl. ............................. 562/19; 556/174
(58) Field of Search ............... 562/19; 556/174; 524/116

(56) References Cited

U.S. PATENT DOCUMENTS

| | | |
|---|---|---|
| 3,594,347 | 7/1971 | Lazarus et al. . |
| 3,892,998 | 7/1975 | Tsui et al. . |
| 3,900,444 | 8/1975 | Racky et al. . |
| 3,953,539 | 4/1976 | Kawase et al. . |
| 4,036,811 | 7/1977 | Noetzel et al. . |
| 4,049,612 | 9/1977 | Sandler . |
| 4,078,016 | 3/1978 | Kramer . |
| 4,180,495 | 12/1979 | Sandler . |
| 4,208,321 | 6/1980 | Sandler . |
| 4,208,322 | 6/1980 | Sandler . |
| 5,194,576 | 3/1993 | Poll et al. . |
| 5,780,534 | 7/1998 | Kleiner et al. . |
| 6,087,423 * | 7/2000 | Kleiner et al. ............... 524/116 |

FOREIGN PATENT DOCUMENTS

| | | |
|---|---|---|
| 700 042 | 7/1967 | (BE) . |
| 2 102 841 | 8/1971 | (DE) . |
| 2 252 256 | 5/1974 | (DE) . |
| 2 252 258 | 5/1974 | (DE) . |
| 2 447 727 | 4/1976 | (DE) . |
| 2 915 116 | 10/1979 | (DE) . |
| 006 568 | 1/1980 | (EP) . |
| 2 827 867 | 1/1980 | (DE) . |
| 452 755 | 10/1991 | (EP) . |
| 458 067 | 11/1991 | (EP) . |
| 498 059 | 8/1992 | (EP) . |
| 699 708 | 3/1996 | (EP) . |
| 794 191 | 9/1997 | (EP) . |
| 2 204 659 | 10/1972 | (FR) . |
| 2 422 698 | 4/1978 | (FR) . |

OTHER PUBLICATIONS

Derwent English Abstract (1971–52012S) for DE 2 102 841 (Aug. 5, 1971).
Derwent English Abstract (1974–C6071V) for DE 2 252 256 (May 9, 1974).
Derwent English Abstract (1974–34563V) for DE 2 252 258 (May 9, 1974).
Derwent English Abstract (1976–28565X) for DE 2 447 727 (Apr. 8, 1976).
Derwent English Abstract (1979–59863B) for DE 2 915 116 (Oct. 25, 1979).
Derwent English Abstract (1980–02156C) for DE 2 827 867 (Jan. 17, 1980).
Derwent English Abstract (1980–02156C) for EP 006 568 (Jan. 9, 1980).
Derwent English Abstract (1991–312047) for EP 452 755 (Oct. 23, 1991).
Derwent English Abstract (1991–347511) for EP 458 067 (Nov. 27, 1991).
Derwent English Abstract (1992–269839) for EP 0 498 059 (Aug. 12. 1992).
Derwent English Abstract (1996–130732) for EP 0 699 708 (Mar. 6, 1996).
Derwent English Abstract (1997–437433) for EP 794 191 (Sep. 10, 1997).
Derwent English Abstract (1974–34563V) for FR 2 204 659 (Oct. 25, 1972).
Derwent English Abstract (1979–59863B) for FR 2 422 698 (Apr. 13, 1978).
Derwent English Abstract (1976–42858X) for JP 51 047035 and JP 82 059262 (Apr. 22, 1976).
English Abstract for BE 700,042 (7/67).

* cited by examiner

*Primary Examiner*—Jean F. Vollano
(74) *Attorney, Agent, or Firm*—Connolly Bove Lodge & Hutz LLP

(57) ABSTRACT

The invention relates to a method for producing aluminum salts of cyclic phopshinic acid. According to the invention, cyclic phosphinic acids, such as 1-hydroxydihydrophosphole oxide or 1-hydroxyphospholane oxide, are reacted with a basic aluminum acetate, such as hydroxyaluminum diacetate, in the presence of water and in the absence of polar solvents with heat for a reaction time of 1 to 20 hours.

17 Claims, No Drawings

METHOD FOR PRODUCING ALUMINIUM SALTS OF CYCLIC PHOSPHINIC ACID

This is the national phase of PCT/EP98/04833 filed Aug. 3, 1998, now WO99/07715.

BACKGROUND OF THE INVENTION

1. Field of the Invention

The invention relates to a process for preparing aluminum salts of saturated or unsaturated cyclic phosphinic acids, in particular aluminum salts of 1-hydroxydihydrophosphole oxides and of 1-hydroxyphospholane oxides.

2. Description of the Prior Art

Salts from phosphinic acids have been known per se for a relatively long time and are recommended in particular as flame-retardant additives for thermoplastics, such as polyesters or polyamides. For example, DE-A1-2252258 describes alkali metal salts of phosphonic acids. However, they have to be added in comparatively large amounts, and in some cases have an adverse corrosion-promoting effect on the processing machinery, EP-A3-0699708 discloses polyester molding compositions which contain calcium phosphinates or aluminum phosphinates of the following formulae:

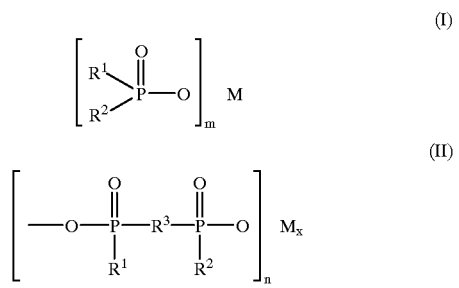

where
$R^1$ and $R^2$ are $C_1$–$C_6$-alkyl, linear or branched, or phenyl;
$R^3$ is $C_1$–$C_{10}$-alkylene, linear or branched, or arylene, or alkylarylene, or arylalkylene;
M is a calcium or aluminum ion;
m is 2 or 3;
n is 1 or 3;
x is 1 or 2

The aluminum salts described in this European patent application and derived from the phosphinic acids also mentioned therein, require for their preparation a comparatively long reaction time, specifically 24, and in some cases even 65, hours.

Although a very large number of compounds derived from phosphinic acids, and preparation processes for these compounds, are already known, there is still a need for improved processes for preparing suitable salts derived from phosphonic acids and capable of being used as agents for improving the flame retardancy of plastics.

It is therefore an object of the invention to provide a process which permits the preparation of useful salts derived from phosphinic acids and capable of being used as flame retardants. Another object of the invention is to provide a process which operates cost-effectively and gives high yields with short reaction times. A further object of the invention is to provide a process which operates in an environmentally sound manner and which gives rise to no, or only very small, amounts of substances which have to be removed and disposed of in isolating the end product.

SUMMARY OF THE INVENTION

This object is achieved by means of a process for preparing aluminum salts of cyclic phosphinic acids, which comprises reacting cyclic phosphinic acids with basic aluminum acetate, such as hydroxyaluminum diacetate, in the presence of water and in the absence of polar solvents, at elevated temperature and with a reaction time of from 1 to 20 hours. The reaction time is preferably from 1 to 10 hours, in particular from 3 to 7 hours. Particularly advantageous reaction temperatures are from 50 to 200° C., in particular from 80 to 100° C. It is advantageous to react 1 mol of acid with ⅓ mol of basic aluminum acetate in the presence of from 0.5 to 4 ml of water, calculated per gram of acid; it is preferable to use from 2 to 3 ml of water per gram of acid.

DESCRIPTION OF THE PREFERRED EMBODIMENTS

The cyclic phosphinic acids used for the reaction with basic aluminum acetate are preferably 1-hydroxydihydrophosphole oxides according to formula 1a or 1b or 1-hydroxyphospholane oxides according to formula 1c, or mixtures of these,

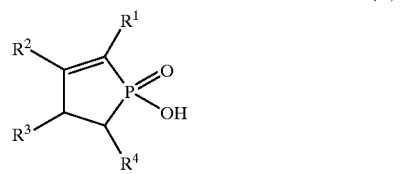

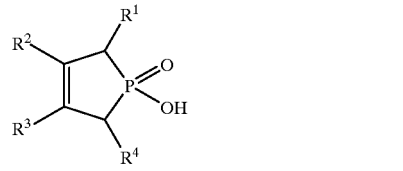

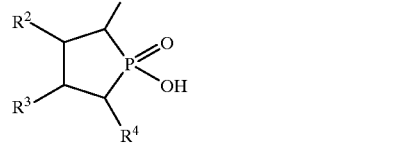

where $R^1$, $R^2$, $R^3$ and $R^4$ are hydrogen or alkyl, preferably $C_1$–$C_{12}$-alkyl, in particular $C_1$–$C_4$-alkyl, preferably methyl or ethyl.

The reaction may be carried out under pressure, preferably in an autoclave under autogenic pressure.

The cyclic phosphinic acids used according to the invention may be obtained by hydrolyzing corresponding cyclic chloro compounds. For example, the preparation of 1-chlorodihydrophosphole oxide and the hydrolysis of this compound to give 1-hydroxydihydrophosphole oxide is described by Kurt Moedritzer in SYN. REACT. INORG. METAL-ORG. CHEM., 5(1), 45–58 (1975). Another synthetic path for preparing chlorine compounds of this type can be found in EP-A1-0452755. The saturated cyclic phosphinic acids may be obtained by hydrogenating the corresponding unsaturated cyclic phosphinic acids.

The corresponding aluminum salts are prepared by dissolving the phosphinic acids in water and reacting them with basic aluminum acetate, preferably hydroxyaluminum diacetate. Even though it is not absolutely essential to carry out the reaction in precise stochiometric ratios, it is nevertheless expedient to use ⅓ mol of basic aluminum acetate per mole of acid. The amount of water used in the reaction may also vary over a wide range. However, it is advantageous to use from about 0.5 to 4 ml, in particular from 2 to 3 ml, of water per gram of acid used.

The reaction is carried out at elevated temperature, and it is advantageous to stir the reaction mixture during the reaction. It is advantageous to ensure that the temperature is maintained at least 50° C., and the temperature range from 50 to 200° C., in particular from 80 to 100° C., is very suitable.

The reaction may also be carried out successfully under pressure, pressures of from 1 to 10 bar, in particular from 1 to 5 bar, being particularly advantageous.

The following compounds, inter alia, have proven to be suitable cyclic phosphinic acids for the novel process:
1-hydroxy-3-methyl-2,5-dihydro-1H-phosphole 1-oxide, 1-hydroxy-3-methyl-1H-phospholane 1-oxide, 1-hydroxy-2,3-dihydro-1H-phosphole 1-oxide, 1-hydroxy-2,5-dihydro-1H-phosphole 1-oxide and 1-hydroxy-1H-phospholane 1-oxide.

According to the invention, the reaction times are generally not more than 20 hours, and are mostly considerably shorter; it is advantageous to carry out the reaction within a period of from 1 to 10 hours, in particular from 3 to 7 hours. It is also very advantageous to carry out the reaction in an autoclave under autogenic pressure, meaning that the reaction components composed of cyclic phosphinic acid, basic aluminum acetate and water are placed into an autoclave and reacted there under autogenic pressure, i.e. the reaction mixture is heated in the autoclave in a closed system, so that the reaction is carried out under the pressure which arises when the temperature increases.

The reaction is carried out without adding polar solvents, such as acetic acid, propionic acid, methanol, ethanol, propanol, butanol, acetone, methyl ethyl ketone, tetrahydrofuran, dioxane or acetonitrile or the like.

It was particularly surprising that the novel process makes it possible to prepare the useful aluminum salts of saturated and unsaturated cyclic phosphinic acids with short reaction times. In contrast to the long reaction times of more than 20 hours required for preparing aluminum salts of non-cyclic phosphonic acids, significantly shorter reaction times can be used according to the invention. A reaction time of at most 7 hours is usually sufficient to obtain a high yield.

The process produces very useful aluminum salts of cyclic phosphinic acids; they can be used in particular as flame retardants for plastics, such as polyamides and in particular polyesters.

Since the reaction requires only 3 components, specifically the phosphinic acid, the basic aluminum acetate and water, the process is also very environmentally sound; there is no requirement for removal and disposal of by-products or of undesirable substances, such as organic solvents. The only requirement is the disposal of the small amounts of acetic acid in aqueous solution which are formed.

The invention will be described in more detail by means of the following examples.

1. An Aluminum Salt of the Isomer Mixture of 1-hydroxy-2,5-dihydro-1H-phoshole 1-oxide and 1-hydroxy-2,3-dihydro-1H-phosphole 1-oxide (4:1)

10.0 g (83.3 mmol) of a mixture of 1-hydroxy-2,5-dihydro-1H-phosphole 1-oxide and 1-hydroxy-2,3-dihydro-1H-phosphole 1-oxide (in a ratio of 4:1) are dissolved in 26.5 ml of water. 4.5 g (27.8 mmol) of hydroxyaluminum diacetate are added at 80° C., and the suspension is stirred at from 85 to 90° C. during the stated reaction time, followed by filtering with suction at about 60° C. and drying at from 140 to 150° C. in a vacuum drying cabinet. This gives the reaction product as a pale yellow powder with an m.p. of >380° C. The percentage yield is determined by weighing the filtrate after evaporation of all of the solvent.

| No. 1 | Reaction time [h] | Yield [g] | Residue in filtrate [g] | Yield [% of theory] |
|---|---|---|---|---|
| a | 7 | 10.4 | 0.1 | 99 |
| b | 20 | 10.5 | 0 | 100 |

2. Aluminum Salt of 1-hydroxy-3-methyl-1H-phospholane 1-oxide 11.0 g (83.3 mmol) of 1-hydroxy-3-methyl-1H-phospholane 1-oxide are dissolved in 26 ml of water. 4.5 g (27.8 mmol) of hydroxyaluminum diacetate are added at 80° C., and the suspension is stirred at from 85 to 90° C. during the stated reaction time, followed by filtering with suction at about 60° C. and drying at 100° C. in a vacuum drying cabinet. This gives the reaction product as a colorless powder with an m.p. of >380° C. The percentage yield is determined by weighing the filtrate after evaporation of all of the solvent.

| No. 2 | Reaction time [h] | Yield [g] | Residue in filtrate [g] | Yield [% of theory] |
|---|---|---|---|---|
| a | 7 | 10.8 | 0.8 | 93 |
| b | 20 | 11.2 | 0.4 | 96 |

3. Aluminum Salt of 1-hydroxy-1H-phospholane 1-oxide 9.83 g (83.3 mmol) of 1-hydroxy-1H-phospholane 1-oxide are dissolved in 26.0 ml of water. 4.5 g (27.8 mmol) of hydroxyaluminum diacetate are added at 80° C., and the suspension is stirred at from 85 to 90° C. during the stated reaction time, followed by filtering with suction at about 60° C. and drying at 140° C. in a vacuum drying cabinet. This gives the reaction product as a colorless powder with an m.p. of >380° C. The percentage yield is determined by weighing the filtrate after evaporation of all of the solvent.

| No. 3 | Reaction time [h] | Yield [g] | Residue in filtrate [g] | Yield [% of theory] |
|---|---|---|---|---|
| a | 7 | 10.0 | 0.6 | 94 |
| b | 20 | 10.3 | 0.3 | 96 |

4. Aluminum Salt of Ethylmethylphosphinic Acid (Comparative Example)

10.0 g (92.5 mmol) of ethylmethylphosphinic acid are dissolved in 26 ml of water. 5.0 g (30.8 mmol) of hydroxyaluminum diacetate are added at 80° C., and the suspension is stirred at from 85 to 90° C. during the stated reaction time, followed by filtering with suction at about 60° C. and drying at from 140 to 150° C. in a vacuum drying cabinet. This gives the reaction product as a colorless powder with an m.p. of >380° C. The percentage yield is determined by weighing the filtrate after evaporation of all of the solvent.

| No. 4 | Reaction time [h] | Yield [g] | Residue in filtrate [g] | Yield [% of theory] |
|---|---|---|---|---|
| a | 7 | 7.4 | 3.1 | 69 |
| b | 20 | 9.3 | 1.3 | 87 |

5. Aluminum Salt of methyl-n-propylphosphinic acid (Comparative Example)

10.0 g (81.9 mmol) of methyl-n-propylphosphinic acid are dissolved in 26 ml of water. 4.4 g (27.3 mmol) of hydroxyaluminum diacetate are added at 80° C., and the suspension is stirred at from 85 to 90° C. during the stated reaction time, followed by filtering with suction at about 60° C. and drying at from 140 to 150° C. in a vacuum drying cabinet. This gives the reaction product as a colorless powder with an m.p. of >380° C. The percentage yield is determined by weighing the filtrate after evaporation of all of the solvent.

| No. 5 | Reaction time [h] | Yield [g] | Residue in filtrate [g] | Yield [% of theory] |
|---|---|---|---|---|
| a | 7 | 3.1 | 7.1 | 29 |
| b | 20 | 6.0 | 3.7 | 63 |

6. Aluminum Salt of n-butylmethylphosphinic Acid (Comparative Example)

10.0 g (73.5 mmol) of n-butylmethylphosphinic acid are dissolved in 16 ml of water. 4.0 g (24.5 mmol) of hydroxyaluminum diacetate are added at 80° C., and the suspension is stirred at from 85 to 90° C. during the stated reaction time, followed by filtering with suction at about 60° C. and drying at from 140 to 150° C. in a vacuum drying cabinet. This gives the reaction product as a colorless powder with an m.p. of >380° C. The percentage yield is determined by weighing the filtrate after evaporation of all of the solvent.

| No. 6 | Reaction time [h] | Yield [g] | Residue in filtrate [g] | Yield [% of theory] |
|---|---|---|---|---|
| a | 7 | 2.4 | 7.7 | 23 |
| b | 20 | 6.3 | 4.1 | 59 |

What is claimed is:

1. A process for preparing an aluminum salt of a cyclic phosphinic acid, which comprises reacting the cyclic phosphinic acid with a basic aluminum acetate, in the presence of water and in the absence of a polar solvent selected from the group consisting of acetic acid, propionic acid, methanol ethanol, propanol, butanol, acetone, methyl ethyl ketone, tetrahydrofuran, dioxane and acetonitrile, at an elevated temperature, with a reaction time of from 1 to 20 hours.

2. The process as claimed in claim 1, wherein the basic aluminum acetate is hydroxyaluminum diacetate.

3. The process as claimed in claim 1, wherein the reaction time is from 1 to 10 hours.

4. The process as claimed in claim 3, wherein the reaction time is from 3 to 7 hours.

5. The process as claimed in claim 1, wherein the reaction is carried out at a temperature of from 50 to 200° C.

6. The process as claimed in claim 5, wherein the temperature is from 80 to 100° C.

7. The process as claimed in claim 1, wherein one mol of the cyclic phosphinic acid is reacted with ⅓ mol of the basic aluminum acetate in the presence of from 0.5 to 4 ml of the water, calculated per gram of the acid.

8. The process as claimed in claim 7, wherein from 2 to 3 ml of the water, calculated per gram of the acid, are used.

9. The process as claimed in claim 1, wherein the cyclic phosphinic acid is a 1-hydroxydihydrophosphole oxide according to formula (Ia) or (Ib) or a 1-hydroxyphospholane oxide according to formula (Ic), or a mixture thereof:

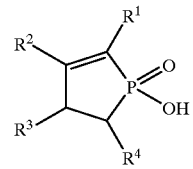

(Ia)

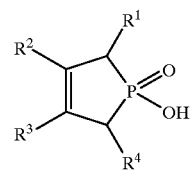

(Ib)

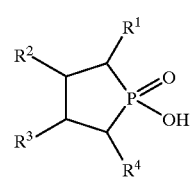

(Ic)

where $R^1$, $R^2$, $R^3$ and $R^4$ are, independently of one another, a hydrogen atom or an alkyl group.

10. The process as claimed in claim 1, wherein the reaction is carried out a pressure of from 1 to 10 bar.

11. The process as claimed in claim 1, wherein the reaction is carried out in an autoclave under an autogenic pressure.

12. The process as claimed in claim 9, wherein the alkyl group is a $C_1$–$C_{12}$-alkyl group.

13. The process as claimed in claim 12, wherein the $C_1$–$C_{12}$-alkyl group is a $C_1$–$C_4$-alkyl group.

14. The process as claimed in claim 13, wherein the $C_1$–$C_4$-alkyl group is a methyl group or an ethyl group.

15. The process as claimed in claim 10, wherein the pressure is from 1 to 5 bar.

16. The process as claimed in claim 9, wherein the cyclic phosphinic acid is 1-hydroxy-3-methyl-2,5-dihydro-1H-phosphole 1-oxide, 1-hydroxy-3-methyl-1H-phospholane 1-oxide, 1-hydroxy-2,3-dihydro-1H-phosphole 1-oxide, 1-hydroxy-2,5-dihydro-1H-phosphole 1-oxide, 1-hydroxy-1H-phospholane 1-oxide or a mixture thereof.

17. The process as claimed in claim 1 wherein the reaction is carried out at a temperature of at least 50° C.

* * * * *

UNITED STATES PATENT AND TRADEMARK OFFICE
CERTIFICATE OF CORRECTION

PATENT NO. : 6,252,108 B1
DATED : June 26, 2001
INVENTOR(S) : Thomas Seitz

Page 1 of 1

It is certified that error appears in the above-identified patent and that said Letters Patent is hereby corrected as shown below:

Title page,
Under References Cited, and U.S. PATENT DOCUMENTS, "4,049,612" should read -- 4,409,612 --.

Signed and Sealed this

Twenty-ninth Day of January, 2002

Attest:

JAMES E. ROGAN
Attesting Officer
Director of the United States Patent and Trademark Office